United States Patent [19]

Cummins

[11] 4,150,225

[45] Apr. 17, 1979

[54] PROCESS FOR PREPARING HERBICIDAL TRIAZINES

[75] Inventor: Earl W. Cummins, Wilmington, Del.

[73] Assignee: E. I. Du Pont de Nemours and Company, Wilmington, Del.

[21] Appl. No.: 864,755

[22] Filed: Dec. 27, 1977

Related U.S. Application Data

[63] Continuation-in-part of Ser. No. 777,323, Mar. 14, 1977, abandoned, which is a continuation-in-part of Ser. No. 677,439, Apr. 15, 1976, abandoned.

[51] Int. Cl.$^2$ ............................................. C07D 251/46
[52] U.S. Cl. .................................... 544/194; 544/211
[58] Field of Search ........................ 544/223, 194, 211

[56] References Cited

U.S. PATENT DOCUMENTS

| | | | |
|---|---|---|---|
| 3,850,924 | 11/1974 | Ruchs et al. | 544/211 |
| 3,907,795 | 9/1975 | Tocker | 544/194 |
| 3,983,116 | 9/1976 | Lin | 544/194 |

*Primary Examiner*—John M. Ford

[57] ABSTRACT

In a process for the preparation of 3-substituted-1-methyl-6-substituted-amino-s-triazine-2,4(1H,3H)-diones by liquid phase cyclization in the presence of an alkali metal alkoxide or hydroxide catalyst of an alkyl-N-(N-substituted carbamoyl-N',N-dialkylamidino)-N-methylcarbamate, by which by-product alkanol, ROH, is formed in the reaction dispersion, the improvement comprising removing the by-product alkanol from the reaction dispersion by vaporization therefrom substantially as it is formed.

5 Claims, No Drawings

PROCESS FOR PREPARING HERBICIDAL TRIAZINES

CROSS-REFERENCE TO RELATED APPLICATIONS

This application is a continuation-in-part of U.S. Pat. application Ser. No. 777,323, filed Mar. 14, 1977, now abandoned, which is a continuation-in-part of U.S. Pat. application Ser. No. 677,439, filed Apr. 15, 1976 and now abandoned.

BACKGROUND OF THE INVENTION

U.S. Pat. No. 3,850,924, filed Apr. 5, 1973, by Julius J. Fuchs and Joel B. Wommack, and granted Nov. 26, 1974, discloses a process for making 3-cyclohexyl-1-methyl-6-dimethylamino-s-triazine-2,4(1H,3H)-dione by the following reaction sequence:

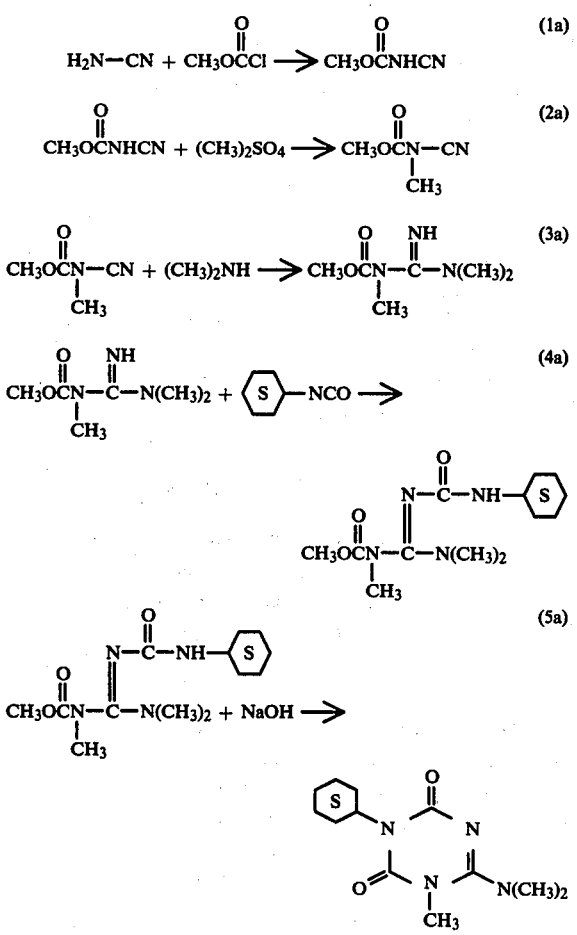

Copending U.S. Pat. application Ser. No. 895,587, filed Apr. 21, 1978 by C. D. Adams et al. discloses an improved process for making such triazinediones wherein significant increases in the practical yield are achieved by utilizing an alkyl chloroformate of the formula

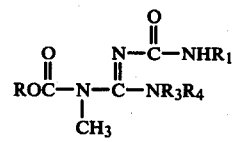

where R = ethyl, n-propyl or isopropyl, in the first reaction step shown immediately above, and, of course carrying the corresponding alkyl substituent through the remainder of the reaction steps.

In the above-referred prior art processes, it was found that the triazine product underwent reaction with the alkanol produced by the cyclization reaction, which caused considerable loss in yield. This side reaction could be reduced to acceptable limits only by the addition of a large excess of dialkylamine to the cyclization reaction system. However, it has now been found that the side reaction can be suppressed by a more efficient and economical procedure, which requires no addition of dialkylamine or any other foreign material which must then be removed in the recovery of purified triazine product.

SUMMARY OF THE INVENTION

In the preparation of 3-substituted-1-methyl-6-substituted-amino-s-triazine-2,4(1H,3H)-diones by liquid phase cyclization in the presence of an alkali metal alkoxide or hydroxide catalyst, $M'OR_5$, of a compound of the formula $$\underset{11}{\underset{CH_3}{\overset{\overset{O}{\underset{\|}{\text{N}-\overset{O}{\underset{\|}{C}}-NHR_1}}}{ROC-N-C-NR_3R_4}}}$$

wherein
R is alkyl of 1–3 carbon atoms;
$R_1$ is selected from alkyl of 2–8 carbon atoms, cycloalkyl of 5–8 carbon atoms, norbornyl, methylcyclopentyl, methylcyclohexyl, phenyl, and chlorophenyl;
$R_3$ is methyl;
$R_4$ is alkyl of 1–4 carbon atoms;
$M'$ is alkali metal;
$R_5$ is hydrogen or alkyl of 1–4 carbon atoms;
by which a by-product alkanol, ROH, is formed in the reaction medium, the improvement comprising conducting the cyclization reaction in the absence of amine $R_3R_4NH$ and removing the by-product alkanol from the reaction medium by vaporization therefrom substantially as it is formed.

DETAILED DESCRIPTION OF THE INVENTION

The improved process of this invention utilizes the reaction of equation I below, in the absence of amine $R_3R_4NH$.

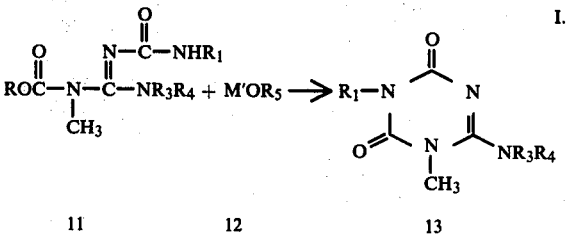

wherein
R is alkyl of 1–3 carbon atoms;
$R_1$ is selected from alkyl of 2–8 carbon atoms, cycloalkyl of 5–8 carbon atoms, norbornyl, methylcyclopentyl, methylcyclohexyl, phenyl, and chlorophenyl;
$R_3$ is methyl;
$R_4$ is alkyl of 1-4 carbon atoms;
$M'$ is alklai metal; and
$R_5$ is hydrogen or alkyl of 1-4 carbon atoms.

The solution containing Compound 11, as prepared by the procedure of either U.S. Pat. No. 3,890,924 or U.S. Ser. No. 675,921, is used as such or compound 11 is isolated by crystallization and mixed with the same or different solvent. Alternatively, the solvent can be exchanged by adding a higher boiling solvent and distilling under reduced pressure so that the pot temperature does not exceed 55° C. Alternatively, a continuous column can be used where the mixed solvent solution is injected into the column, the low boiling solvent is taken overhead, and the solution of compound 11 in the high boiling solvent is taken as bottoms. If the bottoms are cooled rapidly, the column can be operated as high as 90° C. without significant decomposition of compound 11. If solvent exchange is used (using either crystallization or distillation) the new solvent should meet the following criteria:
  (a) the solvent should be inert with respect to the base used to catalyze the cyclization reaction;
  (b) the solvent should allow in the by-product alcohol of Reaction I to be enriched in the overhead upon distillation;
  (c) the solvent should have a solubility of at least 5% for compounds 11 and 13; and
  (d) the solvent should have a boiling point of from 90° C. to 180° C. at atmospheric pressure.

If solvent exchange is not used, the solvent used should meet the following additional criteria:
  (a) the solvent should be unreactive to water, amines and isocyanates;
  (b) the solvent should have only slight solubility in water; and
  (c) the solvent should have a solubility for compound 9 of U.S. Ser. No. 675,921 so that it can be continuously and readily extracted from the reaction mass.

The solution of compound 11, however obtained, is then contacted with the ring closure catalyst (compound 12) to form compound 13 (Equation I). The concentration of compound 11 can vary from 5 to 65%, with 15 to 50% preferred. The initial temperature at which compound 12 is added can vary from 10° C. to the boiling point of the solvent, however, 25° to 80° C. is a preferred range. The ring closure catalyst is an alkali metal alkoxide or hydroxide. Alkali metal alkoxides can be added either as dry solid or as a solution in the alkanol. Alkali metal hydroxides can be added as a solution in an alkanol. A solution of sodium methoxide in methanol is a preferred catalyst.

The amount of catalyst required varies with the purity of the product. When crystalized compound 11 is used, as little as 0.01 mole percent of catalyst may be sufficient to promote ring closure, however, from 0.1 to 1.0 mole percent of catalyst is generally required. When technical material is used, from 1.0 to 4.0 mole percent is generally required. Catalyst in excess of that required to effect complete reaction should be avoided since it also tends to catalyze the formation of by products.

The role of the catalyst in by product formation is illustrated by the following equation:

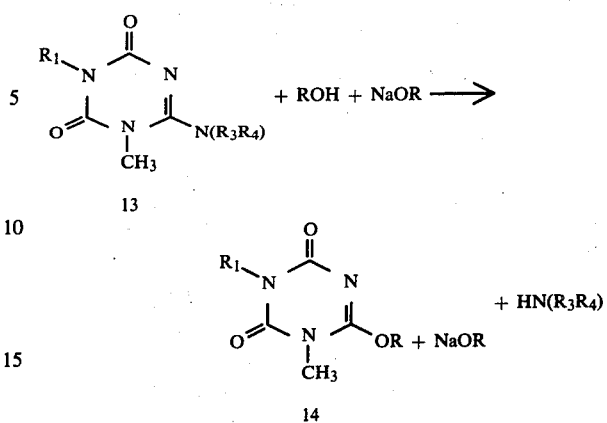

The above equation has been written as if only one alkanol is present in the reaction system. However, if sodium methoxide or a solution of sodium methoxide in methanol were used as catalyst and R groups of compound 11 were ethyl or propyl, obviously a mixture of alkanols would be present.

Compound 14 is an alkylating agent and can react with either the alkanol, catalyst or with by product amine to form compound 15, as follows:

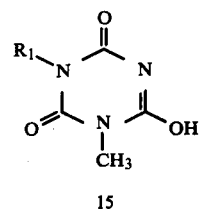

Because this compound is acidic, it reacts with the catalyst to form the corresponding sodium salt, which is inactive. Therefore, when an amount of compound 15 is formed, equivalent to the catalyst added, all reaction ceases.

Obviously, if the formation of compound 13 is complete and all of the catalyst has not been deactivated by formation of compound 15, the reaction to form compound 14 will continue. This can be prevented by the addition of acid to convert the catalyst to an inactive salt. The type of acid used is not critical and can be either organic or inorganic. Organic acids are preferred, particularly acetic acid.

It is difficult to determine the exact time at which the conversion of compound 11 to compound 13 is complete. Premature addition of acid results in incomplete reaction while too late addition results in the formation of even greater amounts of compound 14.

However, this problem can be overcome by adding large amounts (2 to 6 moles based on compound 13) of the amine used in Reaction 3a to the reaction mass before addition of the catalyst. This reduces the yield of compound 14 by converting it back to compound 13 in a dynamic equilibrium as illustrated in the following equation:

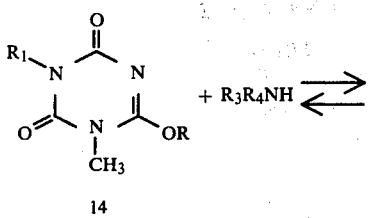

14

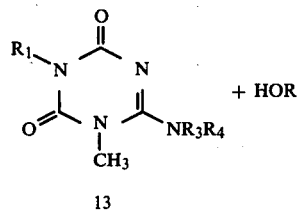

13

Therefore, regardless of how long the reaction is allowed to proceed, only the equilibrium concentration of compound 14 is formed. However, the use of large amounts of amine results in serious process complications. The amine must be fractionated from the reaction mass, condensed (when $R_3$ = methyl and $R_4$ = methyl or ethyl, expensive refrigeration is required) stored and recycled. In addition, there may be pollution problems associated with handling amines.

A superior method of reducing the amount of compound 14 formed during the reaction is to remove the by-product alkanol substantially as it is formed. When this is done, it is no longer available to enter into the reaction with the triazine-dione product to form compound 14 or to react with compound 14 to form compound 15. Therefore, by-product formulation is reduced and less catalyst is required. Furthermore, when essentially all the alkanol is removed, it becomes unnecessary to add acid to terminate the reaction since no further by-products can be formed by reaction with the unconsumed catalyst.

In order to achieve rapid removal of by-product alkanol during the cyclization step, substantially as it is formed, it is, of course, also necessary to mix the catalyst with compound 11 as rapidly as possible. Because good mixing is very difficult to obtain in large-scale batch equipment, it will be recognized by those skilled in mixing operations that continuous mixing will be preferred. Mixing of the cyclization catalyst with compound 11 can be accomplished by mixing in a short residuence time mixer, such as a pipeline mixer, prior to introduction into whatever vaporization means is used. It is preferred that the reaction dispersion of compound 11 and catalyst be passed to the vaporization means within 10-15 milliseconds after initial contact.

Whether a separate mixing step is used or not, it is preferred that the vaporization means be operated in such manner that essentially complete alkanol removal is achieved within about 120 seconds and preferably within no more than about 60 seconds. In a continuous distillation column operation, it is preferred to have a stream of solvent vapor passing up through the column at a rate such that the quantity of overhead product is equal to 0.2-1.2 (preferably 0.4-0.8) times the reaction mass entering the system. By this means, there is sufficient boil-up to accomplish rapid and complete removal of the by-product alkanol. The precise operating temperature and pressures used for vaporization of the alkanol will depend upon the particular reactants and solvents utilized and are thus within the skill of one familiar with the fractionation art.

Though it is not essential to the practice of the invention, it may be preferred to add acid to the dispersion of catalyst after alkanol removal is terminated. In consideration of the rapid rate of the cyclization reaction and alkanol formation, this will normally be subsequent to essential complete removal of the alkanol. This serves (1) to deactivate the catalyst thus preventing the reaction of even trace amounts of alkanol which may still be present, and (2) to prevent decomposition reactions during recovery of the desired compound 13. The amount of acid should be at least about equivalent to the number of moles of catalyst remaining in the system.

Compound 13 is isolated from the liquid residue by conventional procedures, such as the following.

The residue is washed at 30°-100° C., preferably 50°-70° C., with water. If acid has been added to deactivate the catalyst, the residue is washed with 5% aqueous alkali metal hydroxide, preferably sodium hydroxide, in an amount equal to or slightly greater than (up to 20% molar excess) the amount of catalyst, which results in the formation of two liquid layers. After allowing the layers to settle, the lower aqueous layer is removed, and the organic layer is washed with water in an amount approximately equivalent in volume to the caustic wash. Again, the layers are allowed to settle and the aqueous layer is removed. This washing procedure removes by-products formed during the ring-closure reaction. If a less pure product is satisfactory, the washing steps can be eliminated.

The product can be isolated from the organic solvent either after the washing operation or without washing in a number of ways as described below:

(a) The organic phase is concentrated by distillation and is then diluted with a poor solvent for compound 13, e.g., hexane, which causes compound 13 to precipitate. The stable crystalline product is recovered by conventional methods.

(b) The organic phase is concentrated past the solubility limit of compound 13 and is then seeded with crystalline compound 13. An aqueous brine, such as 20% sodium chloride is added, and the organic solvent is boiled off as an aqueous azeotrope at 50-100 mm. Hg. absolute pressure. The aqueous phase of the azeotrope is returned to the vessel. Compound 13 continues to crystallize as the solvent is removed. When solvent removal is complete, the resulting 10-30% slurry is filtered or centrifuged warm at 38°-80°, preferably 40°-45°, washed with water, and the resulting wet cake is dried, thus giving stable crystalline compound 13.

(c) All of the solvent is removed from the organic phase by distillation and sparging with nitrogen or steam at approximately 125°. The compound 13 melt is picked up by a transfer roll and deposited on an agitated, hot (70°-100°, preferably 80°) flaker drum. The flake is then scraped and collected by a heated (60°-80°) screw conveyor. The warm stable crystalline 13 is then permitted to cool to ambient temperature.

(d) Instead of flaking the compound 13 melt described in (c) above, the melt is fed to an agitated, jacketed vessel, such as a "Sigma Arm" mixer, or an agitated, heated fluidized bed of compound 13 crystals, where vigorous agitation is maintained while the temperature is held slightly below the melting point of compound 13, thus giving stable crystalline compound 13. In addition, a solution or slurry of compound 13 can be applied to an agitated, heated fluidized bed of compound 13 crystals. The solvent is permitted to evaporate and the particles of compound 13 increase in both number and size.

In the following examples, all parts are by weight and all temperatures in degrees centigrade unless otherwise indicated.

EXAMPLE I

A. Synthesis of 1-Methyl-3-cyclohexyl-6-dimethylamino-s-triazine-2,4(1H,3H)-dione without alcohol removal - batch operation A 25% solution of sodium methoxide in methanol (16.5 parts) was injected into a well-agitated solution containing 1205 parts of compound 11 (R = ethyl; $R_1$ = cyclohexyl; $R_3$ = $R_4$ = methyl), prepared as described in the Example, section D in said U.S. Ser. No. 574,351, at 50° C. The temperature increased to 58.6° C. in 20 seconds; after an additional 70 seconds, 5.4 parts of glacial acetic acid was added. The solution was then evaporated to dryness in a 50° C. vacuum oven to give 1027 parts of a product that contained 914 parts (89.7% of theory) of compound 13 ($R_1$=cyclohexyl; $R_3$=$R_4$=methyl) by gas chromatographic analysis. This material can be worked up to stable solid product by heating to 125° C. and flaking or by adding to a fluidized bed of compound 13.

B. Synthesis of 1-Methyl-3-cyclohexyl-6-dimethylamino-s-triazine-2,4(1H,3H)-dione with alcohol removal - batch operation A solution containing 1205 parts of compound 11 (R=ethyl; $R_1$=cyclohexyl; $R_3$=$R_4$=methyl) and 2812 parts of toluene was prepared as described in the Example, section D in copending U.S. application Ser. No. 895,587. While being distilled at 111 mm Hg, 11.5 parts of a 25% solution of sodium methoxide in methanol was injected into the reaction mass. The rate of distillation increased rapidly from 35 parts/min to 350 parts/min while the pot temperature dropped from 58.1° to 49.2° in 50 seconds. After an additional 70 seconds, 3.2 parts of acetic acid was added. The solution was then evaporated to dryness in a 50° C. vacuum oven under a nitrogen sparge to give 1025 parts of a product containing 964 (94.6% of theory) parts of compound 13 ($R_1$=cyclohexyl; $R_3$=$R_4$-methyl). This material can be worked up to stable solid product by heating to 125° C. and flaking or by adding to a fluidized bed of compound 13.

EXAMPLE II

Synthesis of 1-Methyl-3-cyclohexyl-6-dimethylamino-s-triazine-2,4(1H,3H)-dione with continuous alcohol removal A solution of 25% wt. of compound 11 (R=ethyl; $R_1$=cyclohexyl; $R_3$=$R_4$-methyl) in toluene at 55°-60° C. was mixed at a rate of 650 ml/min. with 3.0-3.5 ml/min. of an 18% (wt.) solution of sodium methoxide in methanol (1.7-1.9 mole %) at room temperature utilizing a mixing tee. The mixing tee located just outside the top plate of a 6-inch diameter 9-tray sieve plate column, provided turbulent mixing of the two streams, and required less than 50 milliseconds to discharge the mixture to the top tray of the column. The column was operated at 100 mm Hg pressure above the top tray. Toluene was continuously vaporized at the rate of 283 ml/min. outside the column and was introduced into the column as 90° C. vapor below the bottom (9th) tray.

These feed and boil-up rates and temperatures gave about 320 ml/min overhead (distillate) and 620 ml/min bottoms (product) rates. The holdup time of liquid in the column was estimated to be less than 4 minutes. About 5.5 ml/min of glacial acetic acid was added to the product receiver.

The above conditions translate to mass ratios of vapor/feed of 0.40 and distillate/feed of 0.45 and a catalyst level of 2 mole percent based on compound 11.

Analysis of the reaction product by gas chromatography showed the yield of compound 13 was 97.2% of the theoretical yield from compound 11.

EXAMPLE III

Utilizing the same equipment as in Example II, a series of cyclization runs was performed to observe the effect of boil-up/feed ratio on the yield of compound 13 from compound 11. The $R_1$, $R_3$, and $R_4$ substituents of compounds 11 and 13, as well as the cyclization catalyst, were the same as for Example II.

This batch of feed required a higher catalyst level to attain 100% ring-closure. The effect of varying boil-up/feed ratio on compound 13 purity (and hence yield) was examined. Samples of product were drawn at intermediate plates down the column, illustrating the effect of column residence time on ring-closure impurities.

The pertinent conditions and results for each run are summarized in Table I. Runs 1-4 were conducted using 4.7-5.0 mole percent NaOMe.

The results show clearly the advantage of operating the continuous ring-closure process at higher boil-ups and the significant improvements in yield above the batch process.

TABLE I

6-IN. DIA SIEVE-PLATE COLUMN-REACTOR: RUN CONDITIONS & RESULTS
CONTINUOUS F-3456 RING-CLOSURE

P = 100 mm Hg at column head, all runs
Feed on top plate (#1), samples on Plates 3, 7, and product discharge (total 9 plates)
Feed temp = 58°-60° C, toluene vapor 70°-100° C, all runs

| Run No. | Mole % NaOMe | Boil-Up/Feed Ratios | | Res Time Per Plate $\theta_p$ (min) | % R-Closure & % Compound 14 | | | % Compound 13 Yield |
|---|---|---|---|---|---|---|---|---|
| | | Dist/Feed | Vapor/Feed | | Plate 3 | Plate 7 | Product Discharge | |
| 1 | 4.7 | 0.25 | 0.24 | 0.495 | $\frac{100\%}{7.7}$ | $\frac{100\%}{8.8}$ | Void | 91.7 |
| 2 | 4.8 | 0.40 | 0.42 | 0.556 | $\frac{100\%}{4.5}$ | $\frac{100\%}{4.3}$ | $\frac{100\%}{4.5}$ | 95.6 |
| 3 | 4.7 | 0.56 | 0.66 | 0.519 | $\frac{100\%}{2.3}$ | $\frac{100\%}{2.7}$ | $\frac{100\%}{2.4}$ | 97.0 |

TABLE I-continued
6-IN. DIA SIEVE-PLATE COLUMN-REACTOR: RUN CONDITIONS & RESULTS
CONTINUOUS F-3456 RING-CLOSURE P = 100 mm Hg at column head, all runs
Feed on top plate (#1), samples on Plates 3, 7, and product discharge (total 9 plates)
Feed temp = 58°–60° C, toluene vapor 70°–100° C, all runs

| Run No. | Mole % NaOMe | Boil-Up/Feed Ratios Dist/Feed | Vapor/Feed | Res Time Per Plate θp (min) | % R-Closure & % Compound 14 Plate 3 | Plate 7 | Product Discharge | % Compound 13 Yield |
|---|---|---|---|---|---|---|---|---|
| 4 | 5.0 | 0.85 | 1.15 | 0.333 | 100%/2.0 | 100%/1.8 | 100%/Void | 98.1 |

Additional s-traizinediones, which can be prepared by the process of the invention using the appropriate alkoxy-N-(N-substituted carbamoyl-N',N-dialkylamidion)-N-methylcarbamate, are illustrated by the following:

1-Methyl-3-cyclopentyl-6-dimethylamino-s-triazine-2,4(1H,3H)-dione, m.p. 126°–129°

1-Methyl-3-cyclohexyl-6-(N-butyl-N-methylamino)-s-triazine-2,4(1H,3H)-dione

1-Methyl-3-(4-chlorophenyl)-6-dimethylamino-s-triazine-2,4(1H,3H)-dione.

What is claimed is:

1. In a process for the preparation of 3-substituted-1-methyl-6-substituted-amino-s-triazine-2,4(1H,3H)-diones by liquid phase cyclization, in the presence of an alkali metal alkoxide or hydroxide catalyst $M'OR_5$, of a reactant compound of the formula

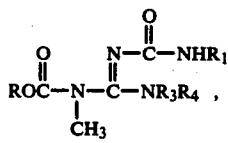

wherein
R is alkyl of 1–3 carbon atoms;
$R_1$ is selected from alkyl of 2–8 carbon atoms, cycloalkyl of 5–8 carbon atoms, norbornyl, methylcyclopentyl, methylcyclohexyl, phenyl, and chlorophenyl;
$R_3$ is methyl;
$R_4$ is alkyl of 1–4 carbon atoms;
M' is alkali metal;
$R_5$ is hydrogen or alkyl of 1–4 carbon atoms, by which by-product alkanol ROH is formed in the reaction dispersion, the improvement comprising conducting the cyclization reaction in the absence of amine $R_3R_4NH$ and removing the by-product alkanol from the reaction dispersion by vaporization therefrom substantially as it is formed.

2. The process of claim 1 in which the removal of by-product alkanol is carried out in a continuous distillation column.

3. The process of claim 2 in which the removal of by-product alkanol from the cyclization reaction product is completed within 120 seconds after the reactant compound and catalyst are contacted.

4. The process of claim 1 in which the reaction product from which by-product alkanol and solvent have been removed is treated with acid in an amount equivalent to at least 1 mole per mole of cyclization catalyst remaining in the reaction product.

5. The process of claim 1 in which the s-triazine reaction product is 1-methyl-3-cyclohexyl-6-dimethylamino-s-triazine-2,4(1H,3H)-dione.

* * * * *